United States Patent [19]

Lee et al.

[11] Patent Number: 4,937,198

[45] Date of Patent: Jun. 26, 1990

[54] NOVEL FLUORESCENT DYE

[75] Inventors: Linda G. Lee, Mountain View, Calif.; Patrick D. Mize, Durham, N.C.

[73] Assignee: Becton, Dickinson and Company, Franklin Lakes, N.J.

[21] Appl. No.: 386,904

[22] Filed: Jul. 28, 1989

[51] Int. Cl.$^5$ .................. G01N 33/533; C07D 473/00
[52] U.S. Cl. ...................................... 436/94; 544/277; 436/800
[58] Field of Search .................. 436/94, 800; 544/277; 536/117

[56] References Cited

U.S. PATENT DOCUMENTS

| | | | |
|---|---|---|---|
| 4,637,988 | 1/1987 | Hinshaw et al. | 436/546 |
| 4,659,678 | 4/1987 | Forrest et al. | 436/512 |
| 4,665,020 | 5/1987 | Saunders | 436/800 |

Primary Examiner—Barry S. Richman
Assistant Examiner—Thalia P. Vassilatos
Attorney, Agent, or Firm—Robert M. Hallenbeck

[57] ABSTRACT

A novel fluorescent dye, PUR-1, having the structural

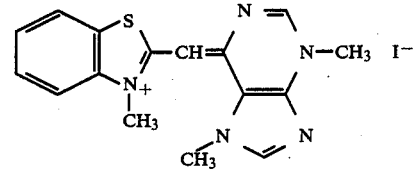

formula is disclosed that will preferentially stain nucleic acids.

15 Claims, 1 Drawing Sheet

NOVEL FLUORESCENT DYE

FIELD OF THE INVENTION

This invention relates to a novel fluorescent dye, and more particularly, relates to a novel fluorescent dye which preferentially stains nucleic acids.

BACKGROUND OF THE INVENTION

Blood-borne parasite infections present a major health problem in many areas of the world. Many of these areas lack both the equipment and skilled technicians to operate the equipment that are available for the detection of such parasites in a biological sample such as blood or a component thereof. In order to combat these problems, certain low-cost and low-skill level instruments have been developed but which provide accurate easily readable results. One such instrument comprises a capillary tube which contains a generally cylindrical mass having a specific gravity such that it will float in one of the cell layers when a blood sample is separated by centrifugation. The mass is selected such that it will form a thin annular space in the tube into which the parasite bearing cells will be crowded, thus increasing the concentration of parasites in a restricted area. The tube then is examined with the aid of a microscope for the presence of parasites within the annular region. U.S. Pat. No. 4,190,328 describes one such device employing this method. Commercially, the QBC ® system (Becton Dickinson Primary Care Diagnostics) embodies this method.

A drawback to this method, however, is that absent the addition of a stain to highlight the presence of the parasite in any given cell the detection of such parasites may be difficult. Parasites may go through several different developmental stages in a particular host. Discriminating between stages is often difficult and requires a certain degree of skill and practice. The presence or absence of a particular stage may be indicative of the relative severity or stage of the infection.

In U.S. Pat. No. 4,190,328, acridine orange is disclosed as a membrane permeable stain that will stain the nucleic acids of parasites. Acridine orange, however, also is permeable in other blood cells and thus will stain to some degree nucleated white blood cells. Thus, where the clinician is not skilled in the identification of the stages of an infection, false positives may occur using a stain like acridine orange.

Another method for the analysis of blood borne parasites is not applicable to field use but is applicable to research use. This method comprises the use of a flow cytometer and a membrane permeable, nucleic acid stain such as thiazole orange. This method recently was described by Makler et al., Cytometry, 8:568 (1987).

Generally, this method comprises isolating a whole blood sample from a patient and staining the cells with thiazole orange. The stained cells then are run through the flow cytometer such as a FACScan ™ (Becton Dickinson Immunocytometry Systems). As the cells pass through the flow cytometer, they pass through a sensing region, substantially one at a time, wherein each cell is scanned by light of excitation wavelength, typically light at 488nm from an argon laser. Light scattered by and fluorescent light emitted from each cell are detected by sensing means, such as photodetectors, and each cell is identified based upon all the light signals detected.

As noted in the reference, background staining of nucleated cells (both immature reds and all stages of whites) will occur as will staining of platelets. Although the staining of white blood cells can be "gated" out of the cell analysis, staining of the nucleated red cells and platelets cannot be gated out and thus will provide background fluorescence which may effect the identification of parasite bearing cells.

Accordingly, what is required for the improved practice of a method such as those described above is a stain that preferentially stains the nucleic acids of blood borne parasites with little or no staining of nucleated red and white blood cells and platelets.

SUMMARY OF THE INVENTION

The present invention comprises a nucleic acid dye which has the general formula:

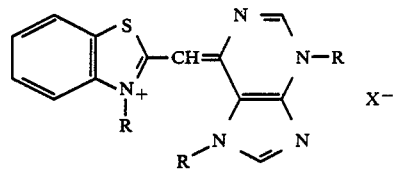

where R is selected from the group consisting of $CH_3$ and $CH_2COO^-$ and $X^-$ is an anion such as a halide, an inorganic ion such as $PO_4^{3-}$, $SO_4^{2-}$, $IO_4^-$, $ClO_4^-$, $NO_3^-$, $NO_2^-$, and the like, or an organic ion such as acetate, glucose-6-phosphate, D-glucuronate and the like. R need not be the same at each position.

The dye is excitable at 488 nm (with maximal excitation at 460 nm) and emits fluorescence in the presence of nucleic acids between 470 to 550 nm with a maximum emission at 478 nm. The dye selectively stains both RNA and DNA nucleic acids.

DETAILED DESCRIPTION

Figure 1:
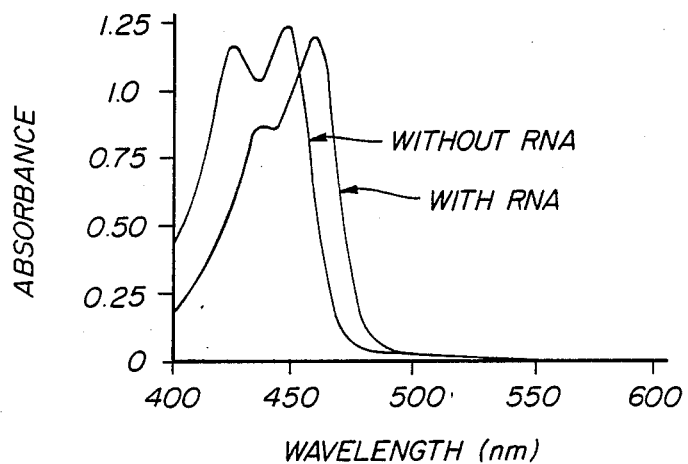
FIG. 1 is a plot of absorbance versus wavelength (nm) for a solution of the iodide salt of PUR-1 with and without RNA.

The present invention comprises a novel fluorescent dye that preferentially will stain the nucleic acids. It is excitable at 488 nm and emits maximally at 478 nm. In the presence of RNA, the fluorescence enhancement of the dye is greater 7,000 fold. The dye has a quantum yield of approximately 0.4.

The dye was synthesized in the following manner which is further set forth in Table I. Unless otherwise specified, all compounds mentioned herein are obtainable from Aldrich Chemical Co. Intermediates 2 and 3 were prepared by minor modification of the methods set forth in Neiman et al., Israel J. Chem. 3:161 (1965). Intermediate 4 was prepared by the method of Brooker et al., J. Am. Chem. Soc., 67:1889 (1945).

Melting points were determined on a Thomas Hoover capillary melting point apparatus and are uncorrected. NMR spectra were recorded on an IBM WP-200SY and chemical shifts were reported relative to tetramethylsilane. Analytical reverse phase ion paired HPLC was performed on a Waters 860 two pump system with photo diode array detection (200–600 nm) using a Brownlee cyano 4.6×220 mm column with the following conditions: initial hold for 5 minutes at 50 mM triethylammonium acetate in water at pH 6.5 followed by a linear gradient to 50 mM triethylammonium acetate in acetonitrile over a 1 hour period. High resolution mass spectra were obtained from Mass Spectrometry Facility of Duke University.

combined and a white crystalline solid formed. This material (3) was combined with the amorphous solid and was used without purification in the synthesis of PUR 1.

Preparation of 2,3-Dimethylbenzothiazolium iodide (4):

4.8 gm of methyl iodide and 5 gm of 2-methylbenzo-

TABLE I

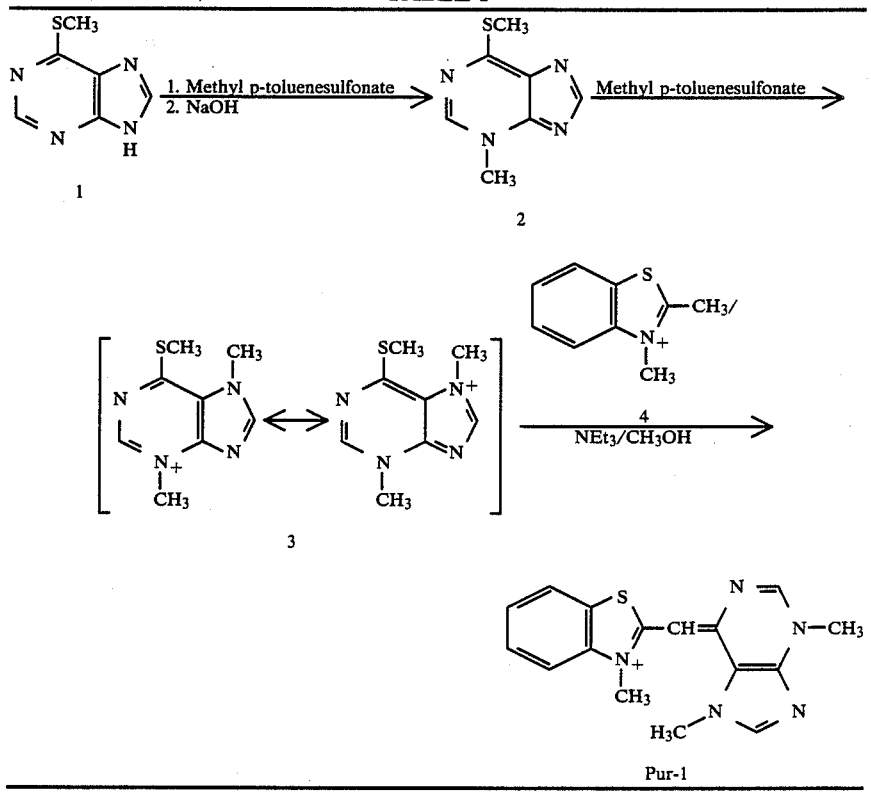

Preparation of 3-Methyl-6-(methylthio)purine (2):

A round bottomed flask was charged with 3 gm of 6(methyltio)purine (1), 3.7 gm of methyl p-toluenesulfonate and 6 ml of diemthylforamide. The mixture was heated in an oil bath at 110° C. for 2.5 hours until it became a clear yellowish solution.

After cooling, 20 ml of water was added to the solution which then was extracted with three 20 ml portions of ether to remove unreacted starting material. The combined ethereal portions were back extracted with 20 ml of water, the aqueous layer was washed with 20 ml ether and then combined with the initial aqueous solution. The solution then was made basic to pH 13 by the addition of KOH. After several minutes, a white crystalline solid precipitate from solution. The solid was filtered and washed with water and air dried. The white crystals were identified as 3 methyl-6-(methylthio)purine (2).

Preparation of 3,7-Dimethyl-6-(methylthio)purine p-toluenesulfonate (3):

A round bottomed flask was charged with 0.80 gm of 3-methyl-6-(methylthio)purine (2) and with 0.95 gm of methyl p-toluenesulfonate. The mixture was briefly heated in an oil bath at 100° C. The homogeneous solution was cooled and then washed with acetone and ether. After washing, the reaction mixture appeared as an amorphous white solid. The organic washes were thiazole were combined in a round bottomed flask equipped with a metal stirring bar and reflux condenser. The flask was heated to 80° C. in an oil bath for 16 hours. The pinkish-white solid (4) was cooled, crushed, washed with acetone and filtered.

Preparation of PUR-1

A round bottomed flask, equipped with a magnetic stirring bar and a reflux condenser, was charged with 1.28 gm of 2,3-dimethylbenzothiazolium iodide (4), approximately 1.50 gm (4.4 mM) of crude 3,7-dimethyl-6-(methylthio)purinium p-toluenesulfonate (3), 20 ml of methanol and 0.5 ml of triethylamine. The mixture was refluxed for about 45 minutes, producing a red solution containing a yellow solid. The material was cooled, filtered and washed with methanol and ether resulting in a yellow-orange solid that was identified by the formula:

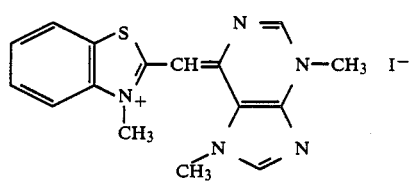

This material was identified as 3-methyl-2-[(3,7-diemthyl-6-purinylidene)-methyl]-benzothiazolium (PUR-1). PUR-1 is the preferred embodiment of the stain and has the following characteristics: mp=340°-345° C.; nmr (CD$_3$OD) δ 3.97 (s, 3H), 3.99 (s, 3H), 4.27 (s, 3H), 6.56 (s, 1H), 7.39 (t, 1H), 7.57 (d, 1H), 7.80 (d, 1H), 8.04 (d, 1H), 8.54 (s, 1H) and 8.85 (s, 1H); HPLC (30 minute retention time for one component), UV max.=448 nm; high resolution FAB-MS for C$_{16}$H$_{16}$N$_{05}$S$_{01}$I$_{01}$ (M+) calculated—310.1126, found —310.1136.

The p-toluenesulfonate salt may be prepared by substituting 2,3-dimethylbenzothiazolium p-toluenesulfonate for 2,3-dimethylbenzothiazolium iodide. The p-toluenesulfonate salt of PUR-1 has the following characteristics when identified by 200MHz NMR spectroscopy: (CD$_3$OD) δ 8.66 (s, 1H); 8.31 (s, 1H); 7.9-7.2 (m, 8H); 6.55 (s, 1H); 4.28 (s, 3H); 4.03 (s, 3H); 3.98 (s, 3H); 2.30 (s, 3H).

Other salt forms may be made from the iodide form by an anion exchange procedure. Briefly, eluent was pumped through a Brownlee Aguapore Anion 10×250 mm column at 2.0 ml/min. The column was flushed with approximately 100 ml of water and was followed by an equilibration with 10 ml of a 1.0M solution of the sodium salt of the anion to be exchanged. Excess buffer was flushed from the column with 200 ml of water. The iodide salt of the stain was injected onto the column and eluted with water of 1:1 solution of water and acetonitrile.

Using this method the following salts of PUR-1 were made as set forth in Table II:

TABLE II

| Equilibrating salt | Eluting Solvent | Final Salt Form |
| --- | --- | --- |
| 1.0 M NaPHO$_4$ | water | (PUR-1)NaPHO$_4$ |
| 1.0 M NaSO$_4$ | water | (PUR-1)NaSO$_4$ |
| 1.0 M Na oxalate | water:acetonitrile | (PUR-1)oxalate |
| 1.0 M Na-D-glucuronate | water:acetonitrile | (PUR-1)-D-glucuronate |

It was found that the PO$_4^{3-}$ and SO$_4^{2-}$ forms of PUR-1 formed by this method were more soluble than the iodide form of PUR-1. Accordingly, it may be more desirable to use these forms PUR-1 than the iodide form when coating capillary tubes into which blood or other blood components later will be added for analysis.

The solubility of the iodide form of PUR-1 also may be improved by substituting CH$_2$COO$^-$ for any or all of the methyl groups attached to nitrogen. This may be accomplished by substituting bromo acetic acid for methyl p-toluenesulfonate in the synthesis compound 3.

Referring to FIG. 1, a 1 mM solution of the p-toluenesulfonate salt of PUR-1 in methanol was prepared. The solution was diluted to a concentration of 2×10$^{-5}$M in phosphate buffered saline ("PBS") or to a concentration of 2×10$^{-5}$M in a solution of PBS containing RNA (torula yeast, Sigma Chemical Co.) at a concentration of 1 mg/ml. The absorbance maximum in the absence of RNA was 448 nm (ε=6.3×10$^4$ M$^{-1}$ cm$^{-1}$), and the absorbance maximum in the presence of RNA was 459 nm (ε=6.0×10$^4$ M$^{-1}$ cm$^{-1}$).

Figure 2:
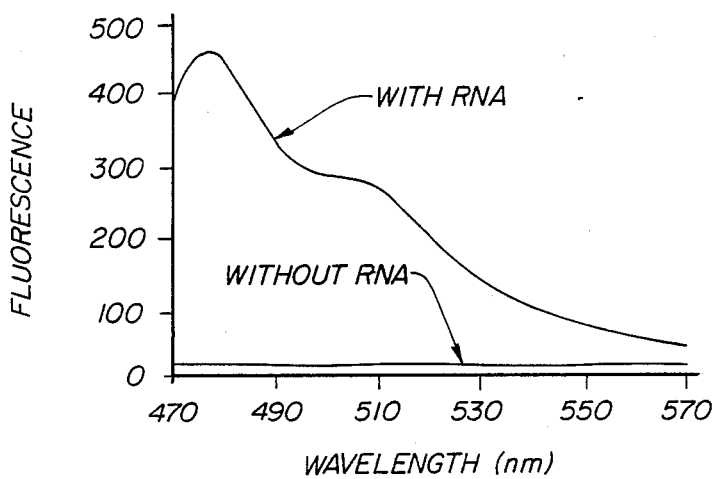
FIG. 2 is a plot of fluorescence versus wavelength for a solution of the p-toluenesulfonate salt of PUR-1 with and without RNA.

Referring to FIG. 2, a solution of PUR-1 in PBS (100 μM) was prepared. To a 3 ml cuvette was added 2.97 ml PBS and 30 ml of the PUR-1 solution. The fluorescence emission of the solution was measured with an excitation wavelength of 460 nm. No fluorescence was observed in the absence of RNA. To a second cuvette was added 2.97 ml of PBS, RNA solution (1 mg/ml, 0.30 ml) and 30 μl of the PUR-1 solution. Fluorescence emission was measured as above. A broad emission curve was measured with a maximum at 478 nm and an approximate quantum yield of 0.4.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A compound having the formula:

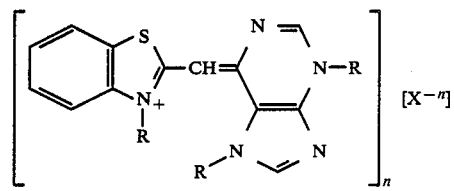

where R is selected from the group consisting of CH$_3$ and CH$_2$COO$^-$, X$^-$ is an anion and n is an integer.

2. The compound of claim 1 wherein R is CH$_3$.

3. The compound of claim 1 wherein R is CH$_2$COO$^-$.

4. The compound of claim 1 wherein the anion is selected from the group consisting of acetate, glucose-6-phosphate and D-glucuronate.

5. The compound of claim 4 wherein X$^-$ is D-glucuronate.

6. The compound of claim 1 wherein said anion is a halide.

7. The compound of claim 6 wherein X$^-$ is I$^-$.

8. The compound of claim 1 wherein said anion is selected from the group consisting of PO$_4^{3-}$, SO$_4^{2-}$, IO$_4^-$, ClO$_4^-$, NO$_3^-$ and NO$_2^-$.

9. The compound of claim 8 wherein X$^-$ is PO$_4^{3-}$.

10. The compound of claim 8 wherein X$^-$ is SO$_4^{2-}$.

11. A method of staining nucleic acids in a biological sample comprising contacting said sample with a compound of claim 1.

12. The method of claim 11 wherein the sample is blood or a component thereof.

13. The method of claim 11 wherein the nucleic acid is RNA.

14. The method of claim 11 wherein the nucleic acid is DNA.

15. A compound having the formula:

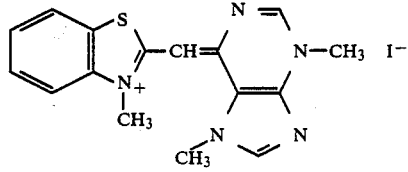

* * * * *